(12) United States Patent
Ueda et al.

(10) Patent No.: US 7,608,280 B2
(45) Date of Patent: Oct. 27, 2009

(54) METHOD OF PRODUCING FR901228

(75) Inventors: Satoshi Ueda, Chuo-ku (JP); Yoko Watamoto, Chuo-ku (JP); Masaru Tsuboi, Chuo-ku (JP); Munekazu Kanda, Chuo-ku (JP); Tomoji Higaki, Chuo-ku (JP); Mitsunori Matsuda, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 12/049,746

(22) Filed: Mar. 17, 2008

(65) Prior Publication Data

US 2008/0227975 A1      Sep. 18, 2008

Related U.S. Application Data

(63) Continuation of application No. 10/362,359, filed as application No. PCT/JP01/07191 on Aug. 22, 2001, now Pat. No. 7,396,665.

(30) Foreign Application Priority Data

Sep. 1, 2000 (JP) .............................. 2000-265414

(51) Int. Cl.
*A61K 9/00* (2006.01)
*A61K 38/12* (2006.01)
*C07K 7/64* (2006.01)

(52) U.S. Cl. ............................ 424/400; 530/317; 514/9

(58) Field of Classification Search ....................... None
See application file for complete search history.

(56) References Cited

U.S. PATENT DOCUMENTS 4,977,138 A    12/1990  Okuhara et al.

| | | |
|---|---|---|
| 6,403,555 B1 | 6/2002 | Skov |
| 6,548,479 B1 | 4/2003 | Skov |
| 7,056,884 B2 | 6/2006 | Nakajima et al. |

FOREIGN PATENT DOCUMENTS

| | | |
|---|---|---|
| EP | 0 352 646 | 1/1990 |
| JP | 4-79892 | 3/1992 |
| WO | WO 01/42282 A1 | 6/2001 |

OTHER PUBLICATIONS

Hirotsugu Ueda, et al., "FR901228, A Novel Antitumor Bicyclic Depsipeptide Produced by *Chromobacterium violaceum* No. 968", I. "Taxonomy, Fermentation, Isolation, Physico-Chemical and Biological Properties, and Antitumor Activity", The Journal of Antibiotics (1994), vol. 47, No. 3, pp. 301-310.

Sshigematsu, et al., "FR901228, A Novel Antitumor Bicyclic Depsipeptide Produced by *chromobacterium violaceum* No. 968", II. "Structure Determination", The Journal of Antibiotics (1994), vol. 47, No. 3, pp. 311-314.

Khan W. Li et al, "Total Synthesis of the Antitumor Depsipeptide FR-901,228", J. Am. Chem. Soc., 1996, 118, pp. 7237-7238.

Material Safety Data Sheet: (E-(1S, 4S, 10S, 21R)-7-[(Z)-ethylidene]4,21-diisopropyl-2-oxa-12,13-dithia-5,8,20,23-tetraaza-3,6,9,19-pentaoxobibyclo[8,7,6]-tricos-16-ene (1993).

*Primary Examiner*—Andrew D Kosar
(74) *Attorney, Agent, or Firm*—Oblon, Spivak, McClelland, Maier & Neustadt, L.L.P.

(57) ABSTRACT

Depsipeptides and congeners thereof are disclosed having structure (I), wherein m, n, p, q, X, R1, R2 and R3 are as defined herein. These compounds, including FR901228, have activity as, for example, immunosuppressants, as well as for the prevention or treatment of patients suffering or at risk of suffering from inflammatory, autoimmune or immune system-related diseases including graft-versus-host disease and enhancement of graft/tissue survival following transplant. Also provided are methods for inhibiting lymphocyte activation, proliferation, and/or suppression of IL-2 secretion. Also provided are crystalline forms of FR901228, e.g., type A and type B crystalline forms of FR901228.

7 Claims, 4 Drawing Sheets

METHOD OF PRODUCING FR901228

CROSS REFERENCE TO RELATED APPLICATIONS

This application is a continuation of U.S. patent application Ser. No. 10/362,359, which is the U.S. National Stage of International Application No. PCT/JP01/07191, filed Aug. 22, 2001, the disclosures of which are incorporated herein by reference in their entireties. This application claims priority to Japanese Patent Application No. JP 2000-265414, filed Sep. 1, 2000, the disclosure of which is incorporated herein by reference in its entirety.

BACKGROUND

The present invention relates to a method of producing FR901228 which is useful as an antibacterial agent and an antitumor agent. More particularly, it relates to a method of producing FR901228 which comprises culturing a FR901228 producing strain in a medium added with at least one amino acid selected from the group consisting of L-arginine, L-histidine, L-cystine and L-cysteine or salt thereof.

FR901228 is a compound produced by culturing a strain belonging to Chromobacterium, e.g., Chromobacterium violaceum WB968 strain (FERM BP-1968) in a nutrient medium, and represented by the following formula (Japanese Patent Publication No. Hei 7 (1995)-64872):

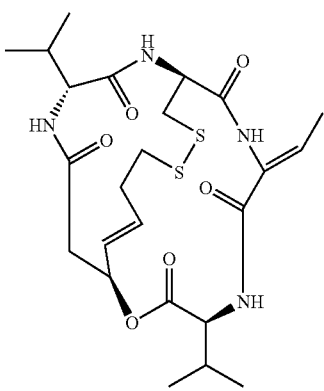

In addition to the fermentation method described above, it is known that FR901228 can also be prepared by semisynthesis or whole synthesis utilizing techniques known in the art (J. Am. Chem. Soc., 118, 7237-7238 (1996)).

FR901228 is known to have a histone deacetylase inhibiting activity (Nakajima, H et al., Experimental Cell Research, 241, 126-133 (1998)), and it has been proposed to expand its utility as an antibacterial agent and an anticancer agent.

However, the fermentation method shows an unsatisfactory production titer of FR901228. Accordingly, it has been demanded a discovery of a strain excellent in FR901228 producing ability or development of a production method capable of increasing the yield of FR901228.

SUMMARY

The inventors of the present invention have noticed the culture conditions for the fermentation method. Upon investigation of the addition of amino acids to a medium, they have found that the addition of specific amino acids represented by L-cysteine unexpectedly increases the yield, though valine or threonine considered to be possible components of FR901228, as well as methionine regarded as effective for production of S-containing compounds do not show increase in yield of FR901228. Thus, the present invention has been achieved.

According to the present invention, provided is a novel fermentation method of producing FR901228, more particularly, a method of producing FR901228 which comprises culturing a FR901228 producing strain in a medium added with at least one amino acid selected from the group consisting of L-arginine, L-histidine, L-cystine and L-cysteine or salt thereof.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF EXEMPLARY EMBODIMENTS

Figure 1:
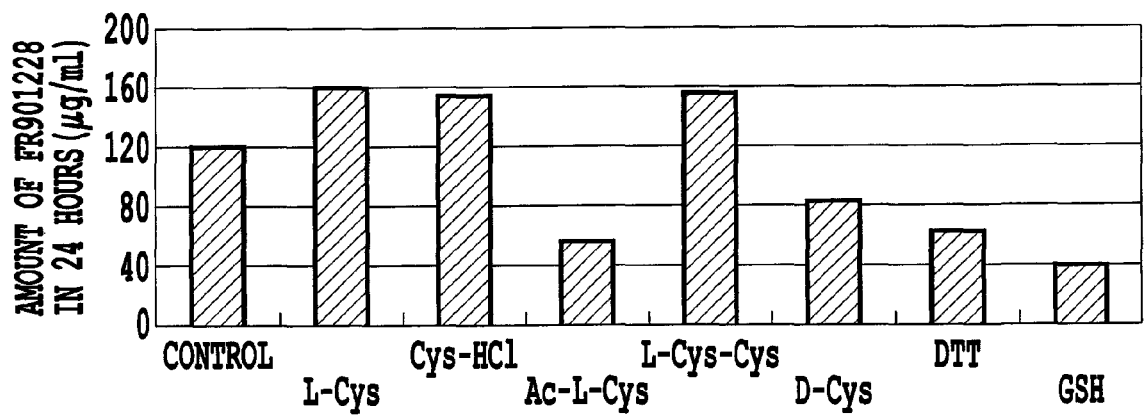
FIG. 1 is a graph for illustrating a comparison of yields of FR901228 in accordance with the addition of various cysteine-related compounds.

As the FR901228 producing strian, used are strains belonging to the above-described Chromobacterium, more specifically, Chromobacterium violaceum WB968 strain (FERM BP-1968: deposited with NIBH on Jul. 20, 1988 under Budapest Treaty). Any other producing strains than the above may be utilized as long as they can produce FR901228. They may be spontaneous mutation strains, or artificial mutation strains obtained by X-ray irradiation, UV irradiation, or treatment with various chemical substances such as N-methyl-N'-nitro-N-nitrosoguanidine, 2-aminopurine and the like.

The amino acid used in the method of the present invention is selected from the group consisting of L-arginine, L-histidine, L-cystine and L-cysteine, which may be singly or in combination of two or more kinds thereof. Further, the amino acid may be in the form of its acid addition salt with an acid such as hydrochloric acid, phosphoric acid, acetic acid, citric acid, succinic acid, lactic acid, tartaric acid, fumaric acid and maleic acid.

An amount of the amino acid added to the medium may vary a little depending on the kind of the amino acid. The amino acid however may be generally added to be its concentration of 2 mM or more, preferably 2 to 30 mM in total with respect to the medium in a volume of 1 liter. With such addition amount, FR901228 is produced in an increased yield.

In case two or more amino acids are mixed, those amino acids may be optionally mixed without any particular limitation to the combination and ratio thereof. However, according to the inventors' experiments, it is confirmed that the addition of L-cysteine shows remarkable increase in the yield of FR901228 as compared with other amino acids that are added individually. Accordingly, where the amino acid mixture is used, it is considered that the yield will be more increased by mixing L-cysteine as one of components of the mixture in a greater mixing ratio.

FR901228 is efficiently produced by culturing the FR901228 producing strain in a nutrient medium containing at least the above-described amino acid and a carbon source and a nitrogen source that can be utilized by the FR901228 producing strain under an aerobic condition.

Examples of the carbon source include glucose, galactose, starch, fructose, dextrin, glycerin, maltose, arabinose, mannose and the like. Examples of the nitrogen source include inorganic or organic nitrogen compounds such as bouillon, yeast extract, peptone, gluten meal, cottonseed flour, soy flour, corn steep liquor, dried yeast, ammonium salts (e.g., ammonium nitrate, ammonium sulfate and ammonium phosphate), or urea and the like.

It is preferred to combine a single carbon source and a single nitrogen source both of high purity, but those of low purity each containing a small amount of a growth factor and a considerable amount of an inorganic nutrient may be used. These sources may properly be used depending on needs.

The above-described medium may contain an inorganic salt such as an alkali metal carbonate (e.g., sodium carbonate, potassium carbonate and the like), an alkali metal phosphate; a magnesium salt (e.g., magnesium sulfate and the like); a copper salt (e.g., cupric nitrate) and a cobalt salt (e.g., cobalt acetate); and liquid paraffin, fatty oil, vegetable oil, mineral oil as well as an antifoaming agent such as silicon and the like, if required.

Preferably, the culture is conducted under deep aerobic condition in a large scale and under shaking or surface culture condition in a small scale. Where the strain is cultured in a large tank, it is preferred to use a preculture of the strain as a seed culture. For example, the preculture may be prepared by inoculating spores or hyphae of the strain in a relatively small amount of a medium and culturing the inoculated medium. In such a case, the medium used for preparing the preculture may substantially be the same as or different from a medium used for production of FR901228 performed later.

During the culture, stirring and aeration may be carried out by various methods known in the art. For example, the stirring may be performed by using various stirrers such as a propeller or a pump equipped with a culture apparatus, or by shaking or rotating the apparatus itself. Alternatively, the stirring and aeration may be performed simultaneously by passing sterilized air in the culture.

The culture may be generally carried out at a temperature in the range of about 10 to 40° C., preferably about 25 to 35° C., for a period of about 15 to 50 hours. The condition may appropriately be varied depending on various factors such as culture scale and the like.

FR901228 obtained by the above-described culture may be isolated and purified by conventional methods, e.g., solvent extraction, concentration under reduced pressure, filtration, pH adjustment, adsorption treatment using an inorganic adsorbent, an adsorption resin or the like, crystallization and the like, or by a combination thereof.

For example, FR901228 is a substance produced in the inside of the strain cells and should be isolated from the strain cells. Accordingly, for easy isolation of FR 901228, pH is adjusted to 1 to 4, preferably 1.5 to 2 by suitably adding an inorganic acid such as sulfuric acid, hydrochloric acid, phosphoric acid, nitric acid or the like; or an organic acid such as citric acid, acetic acid, malic acid, lactic acid or the like to the culture solution.

Examples of the inorganic adsorbent used for the adsorption treatment include silica gel, porous ceramic and the like. As the adsorption resin, DIAION HP10, DIAION HP20, DIAION HP21, DIAION HP40, DIAION HP50 and the like (trademark, manufactured by Mitsubishi Chemical Corporation) may be used.

EXAMPLES

Hereinafter, the production method of the present invention will be explained in detail by way of examples, but the invention is not limited thereto.

Culture:

A medium (20 ml) containing glucose (1%) and bouillon (2%) was put in a 100 ml Erlenmeyer flask, and sterilized at 121° C. for 20 minutes.

A loopful of slant culture of Chromobacterium violaceum WB 968 was inoculated on the medium and cultured at 30° C. for 24 hours on a rotary shaker.

Another medium (20 ml) containing glucose (1% w/v), bouillon (2% w/v), monopotassium phosphate (1.1% w/v), disodium phosphate dodecahydrate (0.72% w/v), ammonium sulfate (0.1% w/v) and magnesium sulfate heptahydrate (0.006% w/v) was put in a 100 ml Erlenmeyer flask and sterilized at 120° C. for 20 minutes. To this medium, a part of the culture obtained above (400 µl) was inoculated. Further, glucose sterilized at 120° C. for 20 minutes (40%, 1 ml) and filter-sterilized (with a membrane filter having pores of 0.45 µm or less) various amino acid solutions (200 mmol/l) or sterilized water containing no amino acid (500 µl) were added to the medium. Then the culture was conducted at 26.5° C. for 48 hours in a rotary shaking culture apparatus.

Example 1

As the amino acid added to the medium in the above-described culture method, L-amino acids of 5 mM/L each described in Table 1 below were used and the influence of the amino acids upon the FR901228 production was examined.

An amount of FR901228 in the culture solution was measured by high performance liquid chromatography (column: Mightysil RP-18 GP (particle size: 3 µm), manufactured by KANTO KAGAKU, 3.0 mm I.D.×150 mm; column temperature: kept constant around 35° C.; detection wavelength: 210 nm; flow rate: 0.3 ml/min; injection amount: 2 µl; mobile phase: THF/acetonitrile/water/phosphoric acid (570:380:50: 1)). The culture solution was centrifuged and the resulting strain was dried and the weight was measured. Thus an amount of dried strain was obtained and its amount with the respect to the culture solution was calculated.

TABLE 1

|  | Amount of FR901228 (µg/ml) | Amount of dried strain (mg/ml) | Amount of FR901228 ($\times 10^3$)/ amount of dried starin |
|---|---|---|---|
| Control (without amino acid) | 151 | 17.8 | 8.5 |
| Arg | 208 | 20.9 | 10.0 |
| His | 204 | 21.4 | 9.5 |
| Cys | 224 | 18.3 | 12.2 |
| Val | 128 | 17.0 | 7.5 |

TABLE 1-continued

|  | Amount of FR901228 (μg/ml) | Amount of dried strain (mg/ml) | Amount of FR901228 (×10³)/ amount of dried starin |
|---|---|---|---|
| Tbr | 150 | 17.0 | 8.9 |
| Gly | 131 | 15.8 | 8.2 |
| Met | 152 | 17.8 | 8.5 |

As shown in Table 1, a yield of FR901228 was increased through the addition of arginine (Arg), histidine (His) or cysteine (Cys). Arginine and histidine also increased the amount of dried starin together with the addition, but cysteine did not show change in the amount of dried strain as compared with the control. Accordingly, the yield per dried strain amount was remarkably high when the cysteine was added.

Unexpectedly, valine (Val), threonine (Thr) and glycine (Gly) that were possible components of FR901228, as well as methionine (Met) which was an amino acid containing a sulfur atom did not show increase in yield of FR901228.

Example 2

In the same manner as in Example 1, various cysteine-related compounds were used to examine the influence of them on the production of FR901228. L-cystine (L-Cys-Cys) was used in a ½ amount.

As a result, L-cysteine (L-Cys), its hydrochloride (Cys.HCl) and L-cystine showed increase in yield of FR901228 as shown in FIG. 1.

Although the cysteine moiety in FR901228 was in the D form, the yield of FR901228 was not increased by addition of D-cysteine (D-Cys). Further, the yield was not increased though dithiothreitol (DTT), reduced glutathione (GSH) or acetylated cysteine compound, i.e., N-acetyl-L-cysteine (Ac-L-Cys), each of which was a compound containing a SH group, was added respectively.

Example 3

Figure 2:
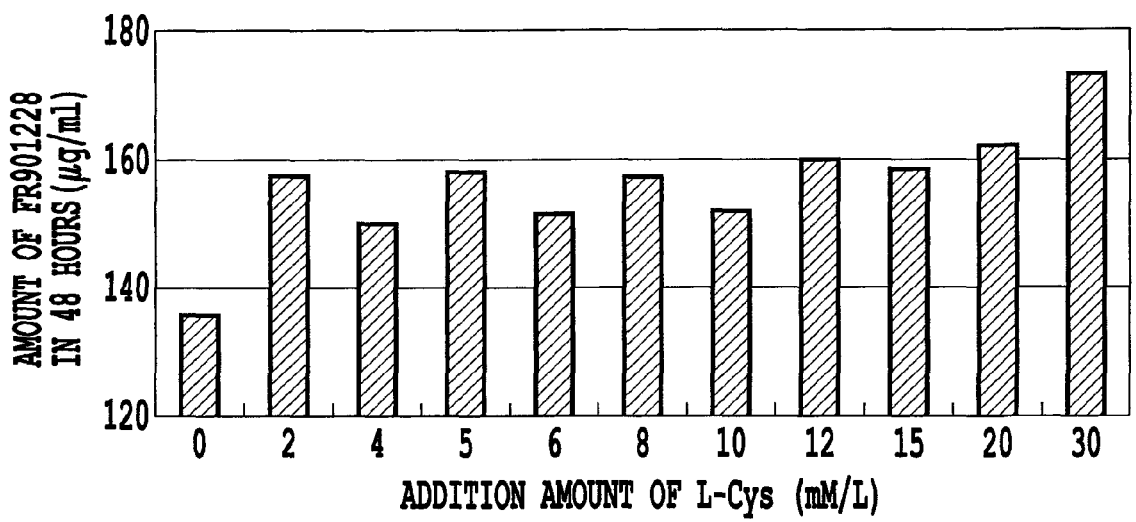
FIG. 2 is a graph for illustrating a result of comparative examination on an optimum concentration of L-cysteine added in a medium.

In the same manner as in Example 1, an optimum concentration of L-cysteine added in the medium was examined and the results shown in FIG. 2 were obtained. Amino acid solution of 500 mmol/L was used.

From the results, it was found that the concentration of L-cysteine in the medium was not directly related to the yield of FR901228.

Example 4

From the control sample without amino acid prepared in Example 1, FR901228 was isolated and purified by the following method.

A culture solution (2190 ml) was prepared in a scale of 100 times greater than that described in the section of Culture. After the culture, pH was adjusted to 2.0 with 1N sulfuric acid and the culture solution was filtrated. The strain was washed with water and the washing water was combined with the filtrate obtained in the previous step. The combined solution (5000 ml) was introduced in a column containing an adsorption resin DIAION HP20 (trademark, manufactured by Mitsubishi Chemical Corporation, 54 ml). The column was washed with water (100 ml) and 25% aqueous acetone (100 ml) and then eluted with 65% aqueous acetone.

The eluate was diluted with water to obtain water content of 70% or higher. The diluted solution (720 ml) was introduced in a column containing DIAION HP20SS (trademark, manufactured by Mitsubishi Chemical Corporation, 40 ml), washed with 40% aqueous acetone (160 ml) and then eluted with 47% aqueous acetone.

The eluate (120 ml) was diluted with water to obtain water content of 70% or higher. Thus obtained solution (200 ml) was introduced in a column of DIAION HP20 (9 ml), washed with 20% aqueous acetone (18 ml) and then eluted with acetone (50 ml). The eluate was concentrated to dryness under reduced pressure and the resulting residue was dissolved in ethyl acetate (3 ml). The solution was introduced in a column of silica gel (silica gel 60, 70-230 mesh, 60 ml), which is previously filled with n-hexane:ethyl acetate (1:1 v/v). The column was developed with n-hexane:ethyl acetate (1:1 v/v, 180 ml) and n-hexane:ethyl acetate (1:2 v/v). Fractions containing FR901228 were combined and concentrated under reduced pressure. The residue was dissolved in acetone (20 ml), which was then added with methanol and concentrated under reduced pressure to obtain FR901228 (250 mg).

Purification-1:

FR901228 (150 mg) was dissolved in 85% ethanol in a concentration of 94 mg/ml. To this solution, water in an amount of 0.8 times greater than that of the solution was added over about 10 minutes (concentration of 52 mg/ml), and then water in an amount of 4.2 times greater was added over about 3 hours (final concentration of about 15 mg/ml). After the total amount of water was added, the precipitate was collected by filtration to give type A crystals of FR901228 (100 mg).

Figure 3:
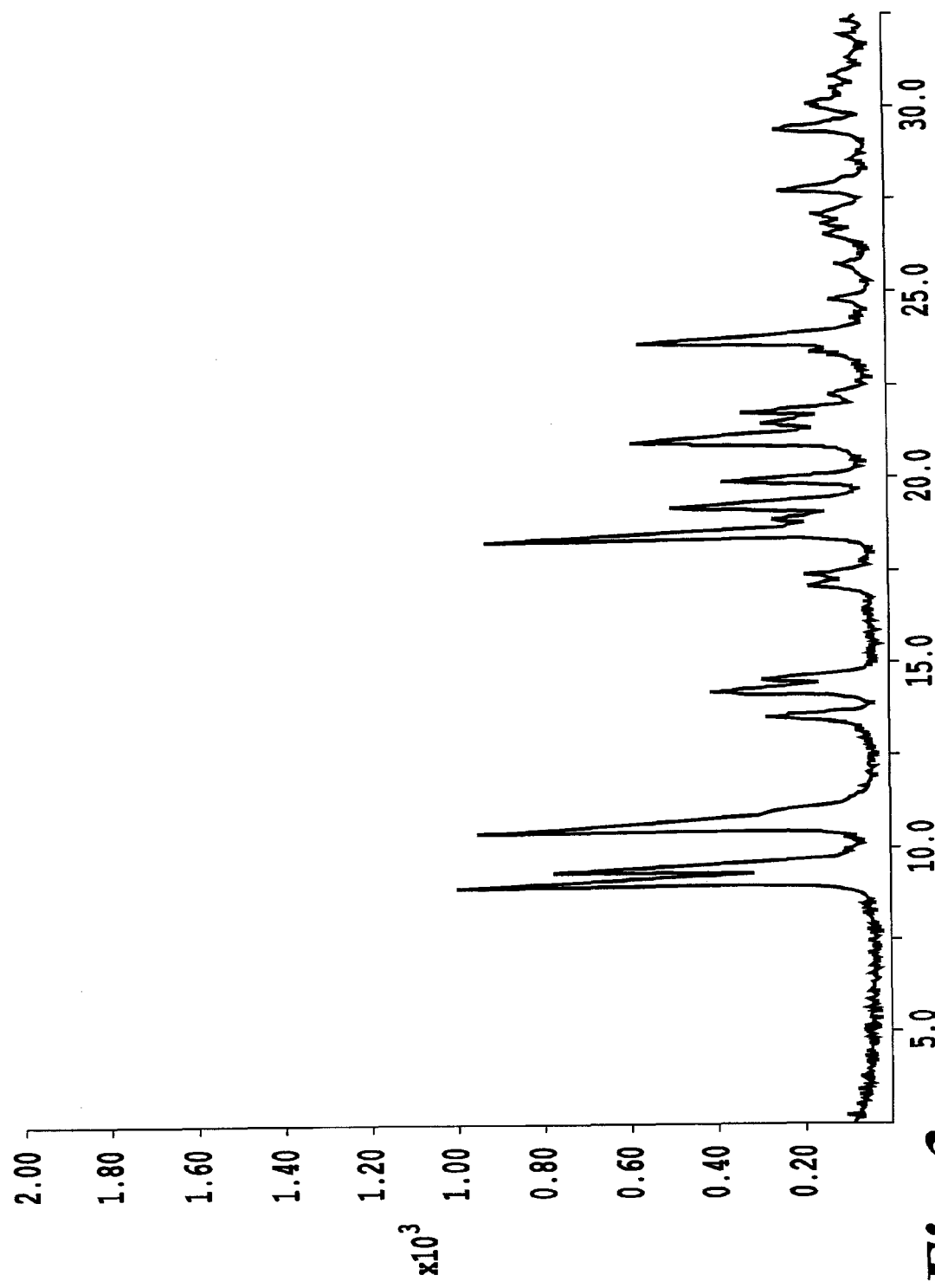
FIG. 3 is a graph for illustrating a result of powder X-ray diffraction analysis of type A crystals (crystals obtained from ethanol/water)

The crystals obtained from ethanol/water were measured by using a powder X-ray diffraction apparatus, Philips MPD 1880 under the following conditions: voltage 40 kv; current 30 mA; Gonio meter PW1775; scanning mode continuous; rate of 0.10 deg/s; distance 0.02 deg; sampling time 0.20 s; DS 1°; RS 0.2 mm; and SS 1°. FIG. 3 shows the results.

Purification-2:

FR901228 (150 mg) was dissolved in 85% aqueous acetone in a concentration of 94 mg/ml. To the solution, water in an amount of 0.8 times greater than that of the solution was added over about 10 minutes (concentration of 52 mg/ml), and then water in an amount of 4.2 times greater was added over about 3 hours (final concentration of about 15 mg/ml). After the total amount of water was added, the precipitate was collected by filtration to give type A crystals of FR901228 (120 mg).

Figure 4:
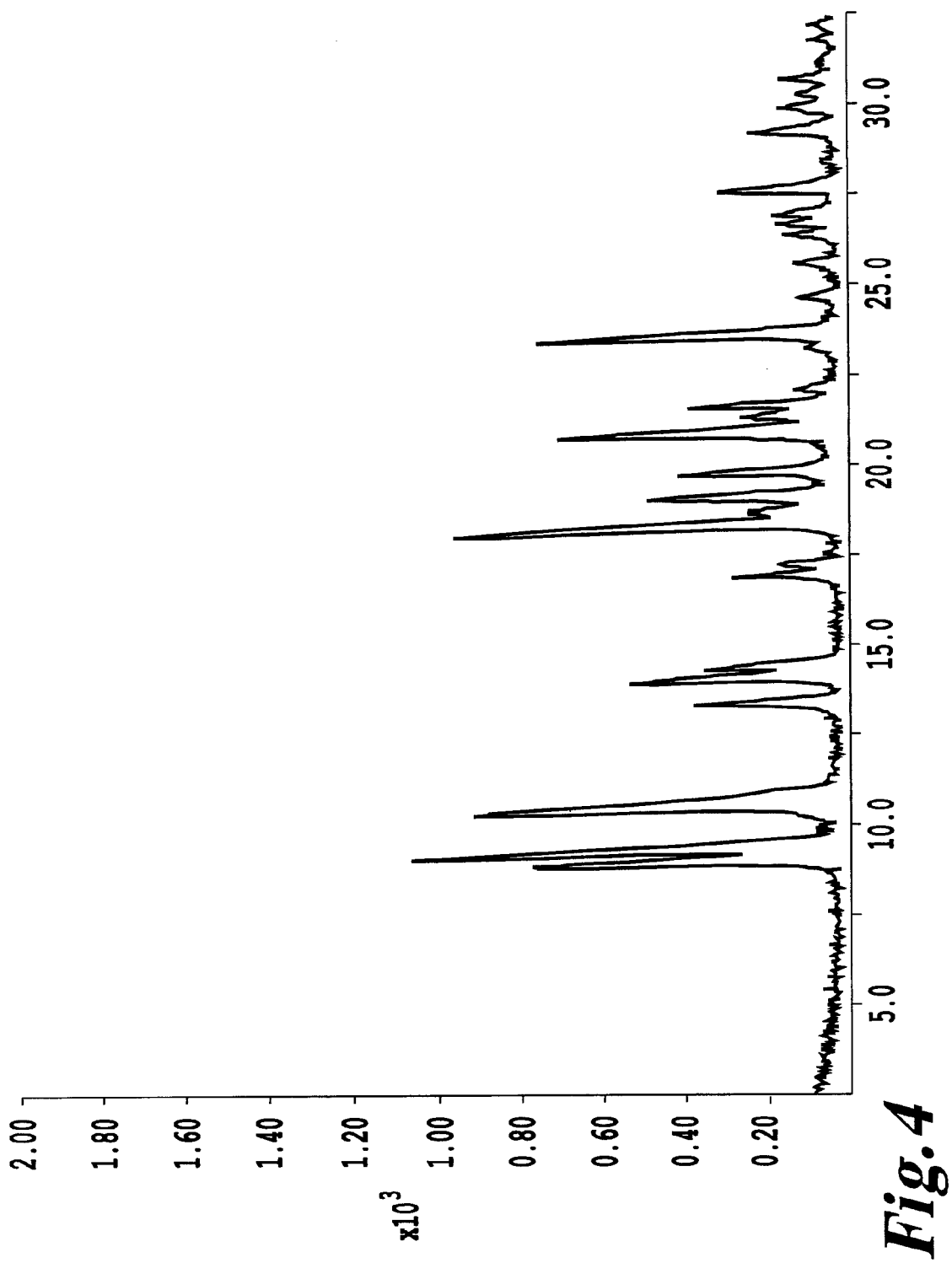
FIG. 4 is a graph for illustrating a result of powder X-ray diffraction analysis of type A crystals (crystals obtained from acetone/water)

The crystals obtained from acetone/water were subjected to the powder X-ray diffraction in the same manner as in Purification-1. FIG. 4 shows the results.

Purification-3:

FR901228 (510 mg) was dissolved in acetone in a concentration of about 11 mg/ml. The solution containing FR901228 was cooled to 5° C. After cooling, n-hexane in an amount equivalent to that of the solution was added over about 20 minutes (concentration of about 5.6 mg/ml) and then n-hexane was added in an amount of 8 times greater than that of the solution over about 70 minutes (final concentration of about 1.2 mg/ml) while maintaining the temperature at 10° C. or lower. After the total amount of n-hexane was added, the precipitate was collected by filtration to give type B crystals of FR901228 (465 mg).

Figure 5:
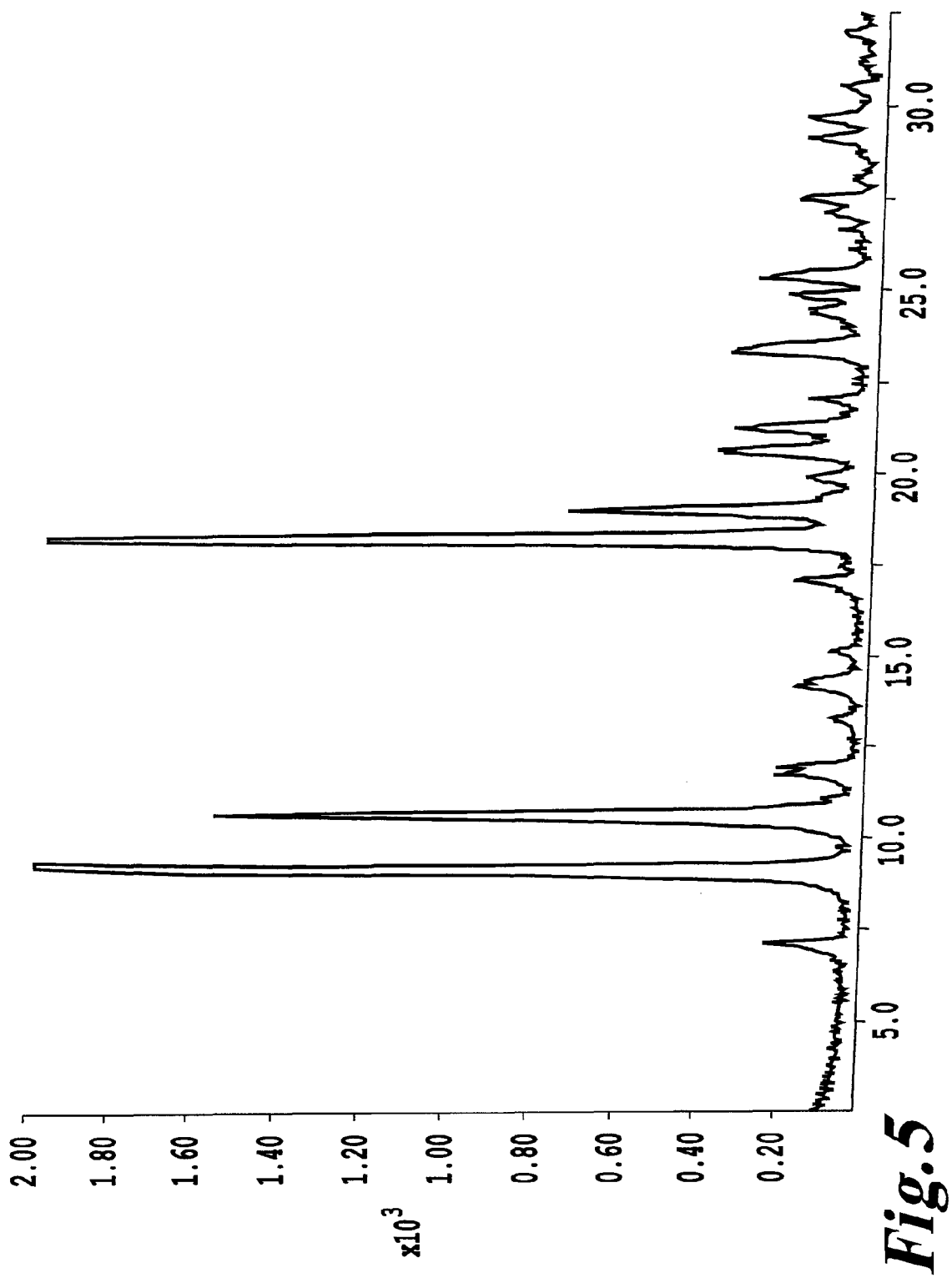
FIG. 5 is a graph for illustrating a result of powder X-ray diffraction analysis of type B crystals.

FIG. 5 shows the results of the powder X-ray diffraction of the type B crystals (diffraction conditions were the same as those in Purification-1).

According to the present invention, provided is a method of producing FR901228 which comprises culturing a FR901228 producing strain in a medium added with at least one amino acid selected from the group consisting of L-arginine, L-histidine, L-cystine and L-cysteine or salt thereof.

According to this method, FR901228 can be produced more efficiently than conventional methods using no amino acid. Therefore, the utilization of FR901228 having high industrial utility value can be further promoted.

In the above detailed description, reference was made by way of non-limiting examples to preferred embodiments of the invention. Obviously, numerous modifications and variations of the present invention are possible in light of the above teachings. It is therefore to be understood that within the scope of the appended claims, the invention may be practiced otherwise than as specifically described herein.

What is claimed is:

1. A type B crystalline form of compound FR901228:

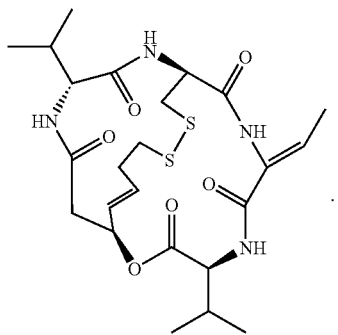

2. The type B crystalline form of claim 1 obtained from hexanes.

3. A type B crystalline form of compound FR901228:

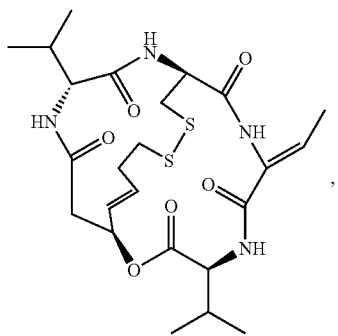

which crystalline form is characterized by a powder X-ray diffraction pattern substantially similar to FIG. 5.

4. A composition comprising a type B crystalline form of compound FR901228:

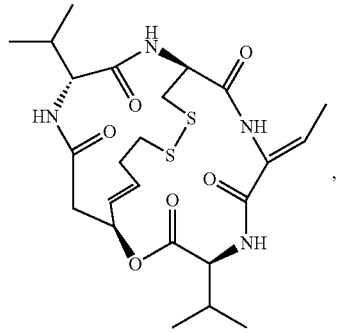

wherein the composition is characterized by having one or more peaks in its X-ray diffraction pattern selected from those at about 7.1, about 11.7, about 11.9, and about 15.1 degrees 2-theta.

5. The composition of claim 4, wherein the composition is characterized by having two or more peaks in its powder X-ray diffraction pattern selected from those at about 7.1, about 11.7, about 11.9, and about 15.1 degrees 2-theta.

6. The composition of claim 4, wherein the composition is characterized by having three or more peaks in its powder X-ray diffraction pattern selected from those at about 7.1, about 11.7, about 11.9, and about 15.1 degrees 2-theta.

7. The composition of claim 4, wherein the composition is characterized by having four peaks in its powder X-ray diffraction pattern at about 7.1, about 11.7, about 11.9, and about 15.1 degrees 2-theta.

* * * * *